(12) United States Patent
Ihara et al.

(10) Patent No.: US 7,371,746 B2
(45) Date of Patent: May 13, 2008

(54) 1,2,4-THIADIAZOLE COMPOUNDS AND PESTS CONTROLLING COMPOSITION CONTAINING THE SAME

(75) Inventors: Hideki Ihara, Osaka (JP); Daisuke Takaoka, Osaka (JP); Hajime Mizuno, Osaka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 80 days.

(21) Appl. No.: 10/567,984

(22) PCT Filed: Sep. 27, 2004

(86) PCT No.: PCT/JP2004/014540

§ 371 (c)(1),
(2), (4) Date: Feb. 10, 2006

(87) PCT Pub. No.: WO2005/037805

PCT Pub. Date: Apr. 28, 2005

(65) Prior Publication Data
US 2007/0004722 A1  Jan. 4, 2007

(30) Foreign Application Priority Data
Oct. 15, 2003 (JP) ............... 2003-354758

(51) Int. Cl.
*A01N 43/82* (2006.01)
*A01N 43/06* (2006.01)
*A01N 43/40* (2006.01)
*C07D 285/08* (2006.01)
*C07D 401/00* (2006.01)
*C07D 295/00* (2006.01)

(52) U.S. Cl. .................. 514/231.2; 514/315; 514/317; 514/231.5; 514/361; 548/128; 548/129; 548/130; 546/184; 546/187; 544/106; 544/98

(58) Field of Classification Search .............. 548/128, 548/130, 129; 546/177, 184, 187; 514/361, 514/299, 315, 317, 231.2, 231.5; 544/106, 544/98

See application file for complete search history.

(56) References Cited

U.S. PATENT DOCUMENTS

| | | | | |
|---|---|---|---|---|
| 5,405,853 A | * | 4/1995 | Baker et al. | 514/299 |
| 6,060,472 A | * | 5/2000 | Karimian et al. | 514/253.1 |
| 6,162,791 A | * | 12/2000 | Karimian et al. | 514/19 |
| 6,468,977 B1 | * | 10/2002 | Karimian et al. | 514/19 |
| 6,858,605 B2 | * | 2/2005 | Solyom et al. | 514/220 |
| 7,300,939 B2 | * | 11/2007 | Kuehnert et al. | 514/253.06 |
| 2005/0215578 A1 | | 9/2005 | Ihara et al. | |
| 2006/0014962 A1 | | 1/2006 | Ihara | |

FOREIGN PATENT DOCUMENTS

| | | |
|---|---|---|
| DE | 30 30 661 A1 | 4/1982 |
| EP | 0116515 * | 8/1984 |
| EP | 0 200 334 A2 | 3/1986 |
| EP | 0 623 604 A2 | 11/1994 |
| JP | 2002/338557 A | 11/2002 |
| WO | WO 2004/041798 A1 | 5/2004 |
| WO | WO 2004/046125 A1 | 6/2004 |

\* cited by examiner

*Primary Examiner*—Sabiha N. Qazi
(74) *Attorney, Agent, or Firm*—Panitch Schwarze Belisario & Nadel LLP

(57) ABSTRACT

The present invention relates to a 1,2,4-thiadiazole compound of the formula (I) represented by the formula (1): wherein $R^1$ represents C3-C7 alkynyl and X represents C4-C7 straight alkylene optionally substituted with one to four of $R^2$, C4-C7 straight alkenylene optionally substituted with one to four of $R^2$, ethylene-oxy-ethylene optionally substituted with one to four of $R^4$, or ethylene-thio-ethylene optionally substituted with one to four of $R^4$, $R^2$ represents a halogen atom, trifluoromethyl or C1-C4 alkyl, and R4 represents a fluorine atom or C1-C3 alkyl. The 1,2,4-thiadiazole compound has an excellent pests controlling activity, and can effectively control an pests such as insect pests, acarine pests and the like

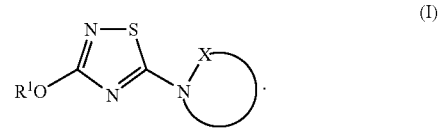

(I)

9 Claims, No Drawings

1,2,4-THIADIAZOLE COMPOUNDS AND PESTS CONTROLLING COMPOSITION CONTAINING THE SAME

CROSS-REFERENCE TO RELATED APPLICATION

This application is a section 371 of International Application No. PCT/JP2004/014540, filed Sep. 27, 2004, which was published in the English language on Apr. 28, 2005, under International Publication No. WO 2005/037805 A2 and the disclosure of which is incorporated herein by reference.

TECHNICAL FIELD

The present invention relates to 1,2,4-thiadiazole compounds and pests controlling composition containing the same.

BACKGROUND ART

Various compounds have been used in the past for the purpose of pest control. Compounds having a 1,2,4-thiadiazole ring are known to have an effect of controlling harmful pests (WO 04/041798).

It is an objective of the present invention to provide novel compounds having a pests controlling effect, pests controlling compositions containing the same compounds, and a method for controlling pests applying effective dose of the same compounds to pests or their habitat.

DISCLOSURE OF INVENTION

The present inventors have intensively studied to find compounds having excellent pests controlling activity, and as a result, found out that the 1,2,4-thiadiazole compounds of formula (I) as depicted below have an excellent controlling activity for pests such as insect pests and acarine pests, thereby completing the present invention.

Namely, the present invention provides the 1,2,4-thiadiazole compound of the formula (I) (hereinafter, referred to as the present compound(s)):

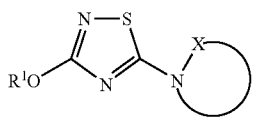

(I)

wherein $R^1$ represents C3-C7 alkynyl; X represents C4-C7 straight alkylene optionally substituted with one to four of $R^2$, C4-C7 straight alkenylene optionally substituted with one to four of $R^2$, ethylene-oxy-ethylene optionally substituted with one to four of $R^4$, or ethylene-thio-ethylene optionally substituted with one to four of $R^4$; $R^2$ represents a halogen atom, trifluoromethyl or C1-C4 alkyl; and $R^4$ represents a fluorine atom or C1-C3 alkyl;

a pests controlling composition containing the present compound as an active ingredient; and a method for controlling pests comprising applying an effective amount of the present compound to pests or habitat of pests.

Furthermore the present invention provides the 1,2,4-thiadiazole compound of the formula (II):

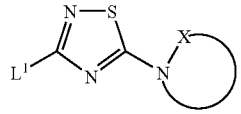

(II)

wherein $L^1$ represents methylsulfinyl or methylsulfonyl; and X has the same meaning as defined above;

which is useful as a intermediate compound for the present compound.

MODE FOR CARRYING OUT THE INVENTION

In this specification;

the C3-C7 alkynyl represented by $R^1$ includes, for example, 2-propynyl, 2-butynyl, 1-methyl-2-butynyl, 2-pentynyl, 4,4-dimethyl-2-pentynyl, 1-methyl-2-propynyl and 1,1-dimethyl-2-propynyl;

the halogen atom represented by $R^2$ includes, for example, a fluorine, chlorine and bromine atom;

the C1-C4 alkyl represented by $R^2$ includes, for example, methyl, ethyl, propyl, isopropyl, sec-butyl and tert-butyl;

the C1-C3 alkyl represented by $R^4$ includes methyl, ethyl, propyl and isopropyl;

the C4-C7 straight alkylene includes tetramethylene, pentamethylene, hexamethylene and heptamethylene;

the C4-C7 straight alkenylene includes, for example, 2-butenylene, 2-pentenpentenylene, 2-hexenylene and 3-hexenylene.

When the C4-C7 straight alkylene or C4-C7 straight alkenylene is substituted with two to four of $R^2$ represented by X, $R^2$s are the same or different. When the ethylene-oxy-ethylene or ethylene-thio-ethylene is substituted with two to four of $R^4$ represented by X, $R^4$s are the same or different.

The substituent depicted by the following formula:

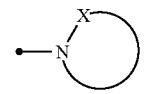

includes, for example, pyrrolidin-1-yl, 2-methylpyrrolidin-1-yl, 2-ethylpyrrolidin-1-yl, 2-propylpyrrolidin-1-yl, 2-isopropylpyrrolidin-1-yl, 2-tert-butylpyrrolidin-1-yl, 2-fluoropyrrolidin-1-yl, 2-trifluoromethylpyrrolidin-1-yl, 3-methylpyrrolidin-1-yl, 3-ethylpyrrolidin-1-yl, 3-trifluoromethylpyrrolidin-1-yl, 2,5-dimethylpyrrolidin-1-yl, 3,4-dimethylpyrrolidin-1-yl, 3,3-dimethylpyrrolidin-1-yl, piperidino, 2-methylpiperidino, 2-ethylpiperidino, 2-propylpiperidino, 2-isopropylpiperidino, 2-tert-butylpiperidino, 2-sec-butylpiperidino, 2-fluoropiperidino, 2-bromopiperidino, 2-trifluoromethylpiperidino, 3-methylpiperidino, 3-ethylpiperidino, 3-propylpiperidino, 3-isopropylpiperidino, 3-tert-butylpiperidino, 3-sec-butylpiperidino, 3-fluoropiperidino, 3-bromopiperidino, 3-trifluoromethylpiperidino, 4-methylpiperidino, 4-ethylpiperidino, 4-propylpiperidino, 4-isopropylpiperidino, 4-tert-butylpiperidino, 4-trifluoromethylpiperidino, 2,6-dimethylpiperidino, 2,4-dimethylpiperidino, 2,5-dimethylpiperidino, 3,5-dimethylpiperidino, 2,2-dimethylpiperidino, 3,3-dimethylpiperidino, 4,4-dimethylpiperidino, 3-ethyl-6-methylpiperidino, 3-ethyl-5-methylpiperidino, 3,5- diethylpiperidino, 3,5-dipropylpiperidino, 3,5-diisopropylpiperidino, 2,3-dimethylpiperidino, 3,3,5-trimethylpiperidino, 2,3,5,6-tetramethylpiperidino, 3,3,5,5-tetramethylpiperidino, 3,3-difluoropiperidino, 4,4-difluoropiperidino, 3-fluoro-3-methylpiperidino, hexamethyleneimino, 2-methylhexamethyleneimino, 2-ethylhexamethyleneimino, 2-propylhexamethyleneimino, 2-isopropylhexamethyleneimino, 2-tert-butylhexamethyleneimino, 3-methylhexamethyleneimino, 3-ethylhexamethyleneimino, 3-propylhexamethyleneimino, 3-isopropylhexamethyleneimino, 4-methylhexamethyleneimino, 4-ethylhexamethyleneimino, 4-propylhexamethyleneimino, 4-isopropylhexamethyleneimino, heptamethyleneimino, 3-pyrrolin-1-yl, 3-methyl-3-pyrrolin-1-yl, 3,4-dimethyl-3-pyrrolin-1-yl, 2,5-dimethyl-3-pyrrolin-1-yl, 1,2,3,6-tetrahydropyridyl, 6-methyl-1,2,3,6-tetrahydropyridyl, 5-methyl-1,2,3,6-tetrahydropyridyl, 4-methyl-1,2,3,6-tetrahydropyridyl, 3-methyl-1,2,3,6-tetrahydropyridyl, 2-methyl-1,2,3,6-tetrahydropyridyl, 2,6-dimethyl-1,2,3,6-tetrahydropyridyl, 2,5,6,7-tetrahydro-1H-azepin-1-yl, 2,3,6,7-tetrahydro-1H-azepin-1-yl, morpholino, 2-methylmorpholino, 2-ethylmorpholino, 3-methylmorpholino, 3-ethylmorpholino, 2,6-dimethylmorpholino, 2,6-diethylmorpholino, 3,3,5,5-tetraethylmorpholino, thiomorpholino and 3,3,5,5-thiomorpholino.

Embodiments of the present compound include, for example, the following compounds:

the 1,2,4-thiadiazole compound of the formula (I) wherein $R^1$ is C3-C7 alkynyl in which the triple bond is located between the carbons of 2 and 3-position;

the 1,2,4-thiadiazole compound of the formula (I) wherein $R^1$ is butynyl;

the 1,2,4-thiadiazole compound of the formula (I) wherein $R^1$ is 2-pentynyl;

the 1,2,4-thiadiazole compound of the formula (I) wherein X is C4-C7 straight alkylene optionally substituted with one to four of $R^2$, C4-C7 straight alkenylene optionally substituted with one to four of $R^2$, or ethylene-oxy-ethylene optionally substituted with one or two of $R^4$, $R^2$ represents a halogen atom, trifluoromethyl or C1-C4 alkyl, and $R^4$ represents C1-C3 alkyl;

the 1,2,4-thiadiazole compound of the formula (I) wherein X is C4-C7 straight alkylene optionally substituted with one to four of $R^2$ or C4-C7 straight alkenylene optionally substituted with one to four of $R^2$;

the 1,2,4-thiadiazole compound of the formula (I) wherein X is ethylene-oxy-ethylene optionally substituted with one to four of $R^4$ or ethylene-thio-ethylene optionally substituted with one to four of $R^4$;

the 1,2,4-thiadiazole compound of the formula (I) wherein X is C4-C7 straight alkylene or C4-C7 straight alkenylene;

the 1,2,4-thiadiazole compound of the formula (I) wherein X is C4-C7 straight alkylene substituted with one or two of $R^2$ or C4-C7 straight alkenylene optionally substituted with one or two of $R^2$;

the 1,2,4-thiadiazole compound of the formula (I) wherein X is C4-C7 straight alkylene optionally substituted with one to four of $R^2$ or C4-C7 straight alkenylene optionally substituted with one to four of $R^2$, and $R^2$ is C1-C4 alkyl;

the 1,2,4-thiadiazole compound of the formula (I) wherein X is C4-C7 straight alkylene optionally substituted with one to four of $R^2$ or C4-C7 straight alkenylene optionally substituted with one to four of $R^2$, and $R^2$ is methyl;

the 1,2,4-thiadiazole compound of the formula (I) wherein X is C4-C7 straight alkylene substituted with one or two of $R^2$ or C4-C7 straight alkenylene optionally substituted with one or two of $R^2$, and $R^2$ is C1-C4 alkyl;

the 1,2,4-thiadiazole compound of the formula (I) wherein X is C4-C7 straight alkylene substituted with one or two of $R^2$ or C4-C7 straight alkenylene optionally substituted with one or two of $R^2$, and $R^2$ is methyl;

the 1,2,4-thiadiazole compound of the formula (I) wherein X is 2,3-dimethyltetramethylene;

the 1,2,4-thiadiazole compound of the formula (I) wherein X is 2,4-dimethylpentamethylene;

the 1,2,4-thiadiazole compound of the formula (I) wherein X is ethylene-oxy-ethylene;

the 1,2,4-thiadiazole compound of the formula (I) wherein X is ethylene-oxy-ethylene substituted with one to four of $R^4$;

the 1,2,4-thiadiazole compound of the formula (I) wherein X is ethylene-oxy-ethylene optionally substituted with one to four of $R^4$, and $R^4$ is methyl;

the 1,2,4-thiadiazole compound of the formula (I) wherein X is ethylene-thio-ethylene;

the 1,2,4-thiadiazole compound of the formula (I) wherein X is ethylene-thio-ethylene substituted with one to four of $R^4$;

the 1,2,4-thiadiazole compound of the formula (I) wherein X is ethylene-thio-ethylene optionally substituted with one to four of $R^4$, and $R^4$ is methyl;

the 1,2,4-thiadiazole compound of the formula (I-1):

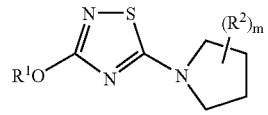

wherein m represents integer of 0 to 4, and $R^1$ and $R^2$ have the same meaning as defined above;

the 1,2,4-thiadiazole compound of the formula (I-1) wherein $R^1$ is C3-C7 alkynyl in which the triple bond is located between the carbons of 2 and 3-position;

the 1,2,4-thiadiazole compound of the formula (I-1) wherein $R^1$ is C3-C7 alkynyl in which the triple bond is located between the carbons of 2 and 3-position, and m is 0;

the 1,2,4-thiadiazole compound of the formula (I-1) wherein $R^1$ is C3-C7 alkynyl in which the triple bond is located between the carbons of 2 and 3-position, and m is 1 or 2;

the 1,2,4-thiadiazole compound of the formula (I-1) wherein $R^1$ is C3-C7 alkynyl in which the triple bond is located between the carbons of 2 and 3-position, m is 1 or 2, and $R^2$ is C1-C4 alkyl;

the 1,2,4-thiadiazole compound of the formula (I-1) wherein $R^1$ is C3-C7 alkynyl in which the triple bond is located between the carbons of 2 and 3-position, m is 1 or 2, and $R^2$ is methyl;

the 1,2,4-thiadiazole compound of the formula (I-2):

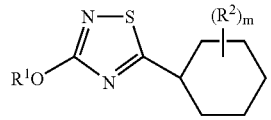

wherein m, $R^1$ and $R^2$ have the same meaning as defined above;

the 1,2,4-thiadiazole compound of the formula (I-2) wherein $R^1$ is C3-C7 alkynyl in which the triple bond is located between the carbons of 2 and 3-position;

the 1,2,4-thiadiazole compound of the formula (I-2) wherein $R^1$ is C3-C7 alkynyl in which the triple bond is located between the carbons of 2 and 3-position, and m is 0;

the 1,2,4-thiadiazole compound of the formula (I-2) wherein $R^1$ is C3-C7 alkynyl in which the triple bond is located between the carbons of 2 and 3-position, and m is 1 or 2;

the 1,2,4-thiadiazole compound of the formula (I-2) wherein $R^1$ is C3-C7 alkynyl in which the triple bond is located between the carbons of 2 and 3-position, m is 1 or 2, and $R^2$ is C1-C4 alkyl;

the 1,2,4-thiadiazole compound of the formula (I-1) wherein $R^1$ is C3-C7 alkynyl in which the triple bond is located between the carbons of 2 and 3-position, m is 1 or 2, and $R^2$ is methyl;

the 1,2,4-thiadiazole compound of the formula (I-3):

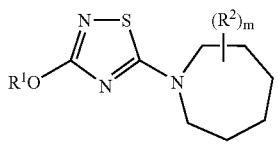

wherein m, $R^1$ and $R^2$ have the same meaning as defined above;

the 1,2,4-thiadiazole compound of the formula (I-3) wherein $R^1$ is C3-C7 alkynyl in which the triple bond is located between the carbons of 2 and 3-position;

the 1,2,4-thiadiazole compound of the formula (I-3) wherein $R^1$ is C3-C7 alkynyl in which the triple bond is located between the carbons of 2 and 3-position, and m is 0;

the 1,2,4-thiadiazole compound of the formula (I-3) wherein $R^1$ is C3-C7 alkynyl in which the triple bond is located between the carbons of 2 and 3-position, and m is 1 or 2;

the 1,2,4-thiadiazole compound of the formula (I-3) wherein $R^1$ is C3-C7 alkynyl in which the triple bond is located between the carbons of 2 and 3-position, m is 1 or 2, and $R^2$ is C1-C4 alkyl;

the 1,2,4-thiadiazole compound of the formula (I-3) wherein $R^1$ is C3-C7 alkynyl in which the triple bond is located between the carbons of 2 and 3-position, m is 1 or 2, and $R^2$ is methyl;

the 1,2,4-thiadiazole compound of the formula (I-4):

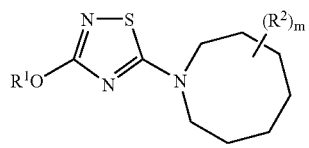

wherein m, $R^1$ and $R^2$ have the same meaning as defined above;

the 1,2,4-thiadiazole compound of the formula (I-4) wherein $R^1$ is C3-C7 alkynyl in which the triple bond is located between the carbons of 2 and 3-position;

the 1,2,4-thiadiazole compound of the formula (I-4) wherein $R^1$ is C3-C7 alkynyl in which the triple bond is located between the carbons of 2 and 3-position, and m is 0;

the 1,2,4-thiadiazole compound of the formula (I-4) wherein $R^1$ is C3-C7 alkynyl in which the triple bond is located between the carbons of 2 and 3-position, and m is 1 or 2;

the 1,2,4-thiadiazole compound of the formula (I-4) wherein $R^1$ is C3-C7 alkynyl in which the triple bond is located between the carbons of 2 and 3-position, m is 1 or 2, and $R^2$ is C1-C4 alkyl;

the 1,2,4-thiadiazole compound of the formula (I-4) wherein $R^1$ is C3-C7 alkynyl in which the triple bond is located between the carbons of 2 and 3-position, m is 1 or 2, and $R^2$ is methyl;

the 1,2,4-thiadiazole compound of the formula (I-5):

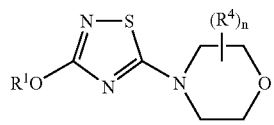

wherein n represents integer of 0 to 4, $R^1$ and $R^4$ have the same meaning as defined above;

the 1,2,4-thiadiazole compound of the formula (I-5) wherein $R^1$ is C3-C7 alkynyl in which the triple bond is located between the carbons of 2 and 3-position;

the 1,2,4-thiadiazole compound of the formula (I-5) wherein $R^1$ is C3-C7 alkynyl in which the triple bond is located between the carbons of 2 and 3-position, and n is 0;

the 1,2,4-thiadiazole compound of the formula (I-5) wherein $R^1$ is C3-C7 alkynyl in which the triple bond is located between the carbons of 2 and 3-position, and n is 1 or 2;

the 1,2,4-thiadiazole compound of the formula (I-5) wherein $R^1$ is C3-C7 alkynyl in which the triple bond is located between the carbons of 2 and 3-position, n is 1 or 2, and $R^4$ is methyl;

the 1,2,4-thiadiazole compound of the formula (I-6):

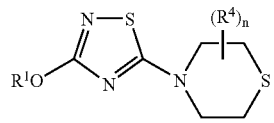

wherein n, $R^1$ and $R^4$ have the same meaning as defined above;

the 1,2,4-thiadiazole compound of the formula (I-6) wherein $R^1$ is C3-C7 alkynyl in which the triple bond is located between the carbons of 2 and 3-position;

the 1,2,4-thiadiazole compound of the formula (I-6) wherein $R^1$ is C3-C7 alkynyl in which the triple bond is located between the carbons of 2 and 3-position, and n is 0;

the 1,2,4-thiadiazole compound of the formula (I-6) wherein $R^1$ is C3-C7 alkynyl in which the triple bond is located between the carbons of 2 and 3-position, and n is 1 or 2;

the 1,2,4-thiadiazole compound of the formula (I-6) wherein $R^1$ is C3-C7 alkynyl in which the triple bond is located between the carbons of 2 and 3-position, n is 1 or 2, and $R^4$ is methyl.

Embodiments of the 1,2,4-thiadiazole compound of the formula (II) include, for example, the following compounds:

the 1,2,4-thiadiazole compound of the formula (II) wherein $L^1$ is methylsulfinyl;

the 1,2,4-thiadiazole compound of the formula (II) wherein $L^1$ is methylsulfonyl;

the 1,2,4-thiadiazole compound of the formula (II) wherein X is C4-C7 straight alkylene optionally substituted with one to four of $R^2$, C4-C7 straight alkenylene optionally substituted with one to four of $R^2$, or ethylene-oxy-ethylene optionally substituted with one or two of $R^4$, $R^2$ represents a halogen atom, trifluoromethyl or C1-C4 alkyl, and $R^4$ represents C1-C3 alkyl;

the 1,2,4-thiadiazole compound of the formula (II) wherein X is C4-C7 straight alkylene optionally substituted with one to four of $R^2$ or C4-C7 straight alkenylene optionally substituted with one to four of $R^2$;

the 1,2,4-thiadiazole compound of the formula (II) wherein X is ethylene-oxy-ethylene optionally substituted with one or two of $R^4$;

the 1,2,4-thiadiazole compound of the formula (II) wherein X is C4-C7 straight alkylene or C4-C7 straight alkenylene;

the 1,2,4-thiadiazole compound of the formula (II) wherein X is C4-C7 straight alkylene substituted with one or two of $R^2$ or C4-C7 straight alkenylene optionally substituted with one or two of $R^2$;

the 1,2,4-thiadiazole compound of the formula (II) wherein X is C4-C7 straight alkylene optionally substituted with one to four of $R^2$ or C4-C7 straight alkenylene optionally substituted with one to four of $R^2$, and $R^2$ is C1-C4 alkyl;

the 1,2,4-thiadiazole compound of the formula (II) wherein X is C4-C7 straight alkylene optionally substituted with one to four of $R^2$ or C4-C7 straight alkenylene optionally substituted with one to four of $R^2$, and $R^2$ is methyl;

the 1,2,4-thiadiazole compound of the formula (II) wherein X is C4-C7 straight alkylene substituted with one or two of $R^2$ or C4-C7 straight alkenylene optionally substituted with one or two of $R^2$, and $R^2$ is C1-C4 alkyl;

the 1,2,4-thiadiazole compound of the formula (II) wherein X is C4-C7 straight alkylene substituted with one or two of $R^2$ or C4-C7 straight alkenylene optionally substituted with one or two of $R^2$, and $R^2$ is methyl;

the 1,2,4-thiadiazole compound of the formula (II) wherein X is ethylene-oxy-ethylene;

the 1,2,4-thiadiazole compound of the formula (II) wherein X is ethylene-oxy-ethylene optionally substituted with one to four of $R^4$, and $R^4$ is methyl;

the 1,2,4-thiadiazole compound of the formula (II) wherein X is ethylene-oxy-ethylene substituted with one or two of $R^4$.

The following will describe a production process for the present compounds.

The present compounds can be produced, for example, by making a 1,2,4-thiadiazole compound of the formula (II) react with an alcohol compound of the formula (III) in the presence of a base;

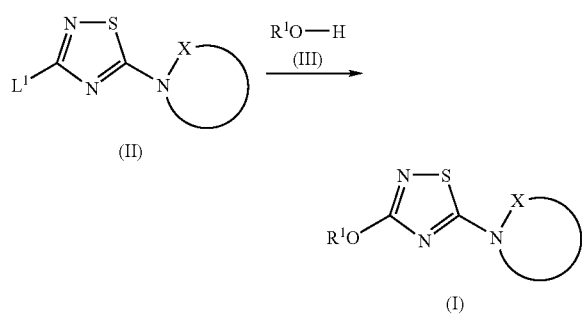

wherein $R^1$, $L^1$ and X have the same meaning as defined above.

The reaction is generally carried out in a solvent.

The solvent to be used in the reaction includes, for example, ethers such as tetrahydrofuran, diethyl ether, tert-butyl methyl ether, ethylene glycol dimethyl ether, 1,4-dioxane and the like, acid amides such as N,N-dimethylformamide and the like, nitriles such as acetonitrile; sulfoxides such as dimethyl sulfoxide; and mixtures thereof.

The base to be used in the reaction includes, for example, alkali metal hydride such as sodium hydride, potassium hydride and the like; carbonates such as potassium carbonate and the like; alkali metal alkoxide such as potassium tert-butoxide, sodium tert-butoxide and the like.

The amount of the base to be used in the reaction is usually 1 to 2 moles, and the amount of the alcohol compound of the formula (III) is usually 1 to 2 moles; relative to 1 mole of the 1,2,4-thiadiazole compound of the formula (II).

The reaction temperature is usually in the range of 0 to 80° C., and the reaction time is usually in the range of 0.5 to 24 hours.

After completion of the reaction, the present compound can be isolated by subjecting the reaction mixture to ordinary post-treatment such as adding the reaction mixture into water, extracting with an organic solvent, concentrating the organic layer obtained; and the like. The isolated present compound can be purified by a technique such as chromatography, recrystallization and the like, if necessary.

The 1,2,4-thiadiazole compound of the formula (II), namely 1,2,4-thiadiazole compound of the formula (II-1) and 1,2,4-thiadiazole compound of the formula (II-2), can be produced, for example, by the following method:

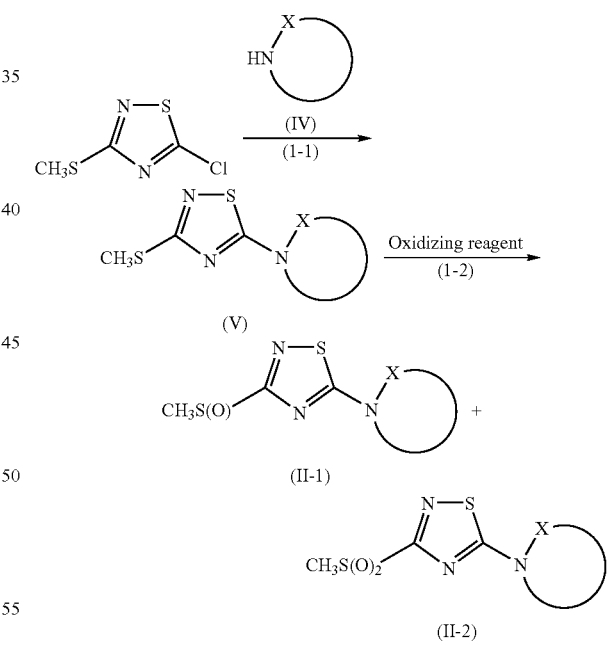

wherein X have the same meaning as defined above.

Process 1-1

The compound of the formula (V) can be produced by making 5-chloro-3-methylthio-1,2,4-thiadiazole react with the compound of the formula (IV).

The reaction is generally carried out in a solvent.

The solvent to be used in the reaction includes, for example, ethers such as tetrahydrofuran, diethyl ether, tert-butyl methyl ether, ethylene glycol dimethyl ether, 1,4- dioxane and the like, acid amides such as N,N-dimethylformamide and the like, nitriles such as acetonitrile; sulfoxides such as dimethyl sulfoxide; alcohols such as methanol, ethanol and the like; and mixtures thereof.

The reaction may be carried out in the presence of a base, if necessary.

The base to be used in the reaction includes, for example, alkali metal hydride such as sodium hydride, potassium hydride and the like; carbonates such as potassium carbonate and the like; and tertiary amines such as triethylamine and the like.

The amount of the compound of the formula (IV) is usually 1 to 2 moles, and the amount of the base is usually 1 to 2 moles; relative to 1 mole of 5-chloro-3-methylthio-1,2,4-thiadiazole.

The reaction temperature is usually in the range of 0 to 80° C., and the reaction time is usually in the range of 0.5 to 24 hours.

After completion of the reaction, the compound of the formula (V) can be isolated by subjecting the reaction mixture to ordinary post-treatment such as adding the reaction mixture into water, extracting with an organic solvent, concentrating the organic layer obtained; and the like. The isolated compound of the formula (V) can be purified by a technique such as chromatography, recrystallization and the like, if necessary.

Process 1-2

The 1,2,4-thiadiazole compound of the formula (II-1) and 1,2,4-thiadiazole compound of the formula (II-2) can be produced by making the compound of the formula (V) react with an oxidizing reagent.

The reaction is generally carried out in a solvent.

The solvent to be used in the reaction includes, for example, chlorinated hydrocarbons such as dichloromethane, chloroform and the like; and water.

The oxidizing reagent to be used in the reaction includes, for example, peroxycarboxylic acids such as 3-chloroperbenzoic acid and the like, and hydrogen peroxide.

The theoretical amount of the oxidizing reagent to produce the 1,2,4-thiadiazole compound of the formula (II-1) is 1 mole, and the theoretical amount of the oxidizing reagent to produce the 1,2,4-thiadiazole compound of the formula (II-2) is 2 mole relative to 1 mole of the compound of the formula (V). But usually the 1,2,4-thiadiazole compound of the formula (II-1) and 1,2,4-thiadiazole compound of the formula (II-2) are produced with a mixture thereof. The 1,2,4-thiadiazole compound of the formula (II-1) and 1,2,4-thiadiazole compound of the formula (II-2) can be separated by a technique such as column chromatography and the like.

The reaction temperature is usually in the range of −20 to 30° C., and the reaction time is usually in the range of 0.05 to 24 hours.

After completion of the reaction, the mixture of the 1,2,4-thiadiazole compound of the formula (II-1) and 1,2,4-thiadiazole compound of the formula (II-2) can be isolated by subjecting the reaction mixture to ordinary post-treatment such as adding the reaction mixture into water, extracting with an organic solvent, washing the organic layer with an aqueous solution of reducing reagent such as sodium sulfite and sodium thiosulfate, concentrating the organic layer obtained and the like.

The mixture of the 1,2,4-thiadiazole compound of the formula (II-1) and the 1,2,4-thiadiazole compound of the formula (II-2) can also be used as the intermediate for the production of the present compound.

Also the 1,2,4-thiadiazole compound (II), namely 1,2,4-thiadiazole compound of the formula (II-1) and 1,2,4-thiadiazole compound of the formula (II-2), can be produced by the following method:

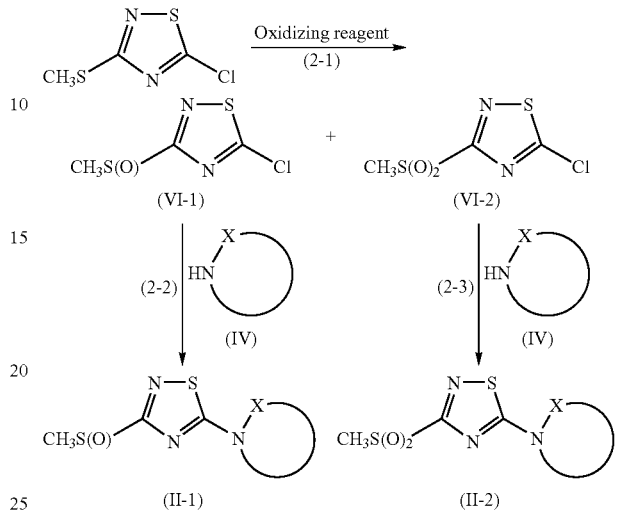

wherein X have the same meaning as defined above.

Process 2-1

The compound of the formula (VI-1) and the compound of the formula (VI-2) can be produced by making 5-chloro-3-methylthio-1,2,4-thiadiazole react with an oxidizing reagent.

The reaction is generally carried out in a solvent.

The solvent to be used in the reaction includes, for example, chlorinated hydrocarbons such as dichloromethane, chloroform and the like; and water.

The oxidizing reagent to be used in the reaction includes, for example, peroxycarboxylic acids such as 3-chloroperbenzoic acid and the like, and hydrogen peroxide.

The theoretical amount of the oxidizing reagent to produce the compound of the formula (VI-1) is 1 mole, and the theoretical amount of the oxidizing reagent to produce the compound of the formula (VI-2) is 2 mole relative to 1 mole of 5-chloro-3-methylthio-1,2,4-thiadiazole. But usually the compound of the formula (VI-1) and compound of the formula (VI-2) are produced with a mixture thereof. The compound of the formula (VI-1) and compound of the formula (VI-2) can be separated by a technique such as column chromatography and the like.

The reaction temperature is usually in the range of −20 to 30° C., and the reaction time is usually in the range of 0.05 to 24 hours.

After completion of the reaction, the mixture of the compound of the formula (VI-1) and compound of the formula (VI-2) can be isolated by subjecting the reaction mixture to ordinary post-treatment such as adding the reaction mixture into water, extracting with an organic solvent, washing the organic layer with an aqueous solution of reducing reagent such as sodium sulfite and sodium thiosulfate, concentrating the organic layer obtained and the like.

The mixture of the compound of the formula (VI-1) and compound of the formula (VI-2) can also be used as the intermediate for the next process.

Process 2-2

The 1,2,4-thiadiazole compound of the formula (II-1) can be produced by making the compound of the formula (VI-1) react with the compound of the formula (IV).

The reaction is generally carried out in a solvent.

The solvent to be used in the reaction includes, for example, ethers such as tetrahydrofuran, diethyl ether, tert-butyl methyl ether, ethylene glycol dimethyl ether, 1,4-dioxane and the like, acid amides such as N,N-dimethylformamide and the like, nitriles such as acetonitrile; sulfoxides such as dimethyl sulfoxide; alcohols such as methanol, ethanol and the like; and mixtures thereof.

The reaction may be carried out in the presence of a base, if necessary.

The base to be used in the reaction includes, for example, alkali metal hydride such as sodium hydride, potassium hydride and the like; carbonates such as potassium carbonate and the like.

The amount of the compound of the formula (IV) is usually 1 to 2 moles, and the amount of the base is usually 1 to 2 moles; relative to 1 mole of the compound of the formula (VI-1).

The reaction temperature is usually in the range of 0 to 80° C., and the reaction time is usually in the range of 0.5 to 24 hours.

After completion of the reaction, the compound of the formula (II-1) can be isolated by subjecting the reaction mixture to ordinary post-treatment such as adding the reaction mixture into water, extracting with an organic solvent, concentrating the organic layer obtained; and the like. The isolated compound of the formula (II-1) can be purified by a technique such as chromatography, recrystallization and the like, if necessary.

Process 2-3

The 1,2,4-thiadiazole compound of the formula (II-2) can be produced by making the compound of the formula (VI-2) react with the compound of the formula (IV).

The reaction is generally carried out in a solvent.

The solvent to be used in the reaction includes, for example, ethers such as tetrahydrofuran, diethyl ether, tert-butyl methyl ether, ethylene glycol dimethyl ether, 1,4-dioxane and the like, acid amides such as N,N-dimethylformamide and the like, nitriles such as acetonitrile; sulfoxides such as dimethyl sulfoxide; alcohols such as methanol, ethanol and the like; and mixtures thereof.

The reaction may be carried out in the presence of a base, if necessary.

The base to be used in the reaction includes, for example, alkali metal hydride such as sodium hydride, potassium hydride and the like; carbonates such as potassium carbonate and the like.

The amount of the compound of the formula (IV) is usually 1 to 2 moles, and the amount of the base is usually 1 to 2 moles; relative to 1 mole of the compound of the formula (VI-2).

The reaction temperature is usually in the range of 0 to 80° C., and the reaction time is usually in the range of 0.5 to 24 hours.

After completion of the reaction, the compound of the formula (II-2) can be isolated by subjecting the reaction mixture to ordinary post-treatment such as adding the reaction mixture into water, extracting with an organic solvent, concentrating the organic layer obtained; and the like. The isolated compound of the formula (II-2) can be purified by a technique such as chromatography, recrystallization and the like, if necessary.

The examples of the present compound are listed below. The 1,2,4-thiadiazole compound of the formula (I) wherein $R^1$ is 2-propynyl and X is one selected from Group (A) below.

Group (A):

tetramethylene, 1-methyltetramethylene, 1-ethyltetramethylene, 1-propyltetramethylene, 1-isopropyltetramethylene, 1-tert-butyltetramethylene, 1-fluorotetramethylene, 1-trifluoromethyltetramethylene, 2-methyltetramethylene, 2-ethyltetramethylene, 2-trifluoromethyltetramethylene, 1,4-dimethyltetramethylene, 2,3-dimethyltetramethylene, 2,2-dimethyltetramethylene, pentamethylene, 1-methylpentamethylene, 1-ethylpentamethylene, 1-propylpentamethylene, 1-isopropylpentamethylene, 1-tert-butylpentamethylene, 1-sec-butylpentamethylene, 1-fluoropentamethylene, 1-bromopentamethylene, 1-trifluoromethylpentamethylene, 2-methylpentamethylene, 2-ethylpentamethylene, 2-propylpentamethylene, 2-isopropylpentamethylene, 2-tert-butylpentamethylene, 2-sec-butylpentamethylene, 2-fluoropentamethylene, 2-bromopentamethylene, 2-trifluoromethylpentamethylene, 3-methylpentamethylene, 3-ethylpentamethylene, 3-propylpentamethylene, 3-isopropylpentamethylene, 3-tert-butylpentamethylene, 3-trifluoromethylpentamethylene, 1,5-dimethylpentamethylene, 1,3-dimethylpentamethylene, 1,4-dimethylpentamethylene, 2,4-dimethylpentamethylene, 1,1-dimethylpentamethylene, 2,2-dimethylpentamethylene, 3,3-dimethylpentamethylene, 2-ethyl-5-methylpentamethylene, 2-ethyl-4-methylpentamethylene, 2,4-diethylpentamethylene, 2,4-dipropylpentamethylene, 2,4-diisopropylpentamethylene, 1,2-dimethylpentamethylene, 2,2,4-trimethylpentamethylene, 1,2,4,5-tetramethylpentamethylene, 2,2,4,4-tetramethylpentamethylene, 2,2-difluoropentamethylene, 3,3-difluoropentamethylene, 2-fluoro-2-methylpentamethylene, hexamethylene, 1-methylhexamethylene, 1-ethylhexamethylene, 1-propylhexamethylene, 1-isopropylhexamethylene, 1-tert-butylhexamethylene, 2-methylhexamethylene, 2-ethylhexamethylene, 2-propylhexamethylene, 2-isopropylhexamethylene, 3-methylhexamethylene, 3-ethylhexamethylene, 3-propylhexamethylene, 3-isopropylhexamethylene, heptamethylene, ethylene-oxy-ethylene, 1-methylethylene-oxy-ethylene, 1-ethylethylene-oxy-ethylene, 2-methylethylene-oxy-ethylene, 2-ethylethylene-oxy-ethylene, 1-methylethylene-oxy-2-methylethylene and 1-ethylethylene-oxy-2-ethylethylene, 2,2-dimethylethylene-oxy-1,1-dimethylethylene, ethylene-thio-ethylene, and 2,2-dimethylethylene-thio-1,1-dimethylethylene.

The 1,2,4-thiadiazole compound of the formula (I) wherein $R^1$ is 2-butynyl and X is one selected from Group (A) described above.

The 1,2,4-thiadiazole compound of the formula (I) wherein $R^1$ is 1-methyl-2-butynyl and X is one selected from Group (A) described above.

The 1,2,4-thiadiazole compound of the formula (I) wherein $R^1$ is 2-pentynyl X is one selected from Group (A) described above.

The pests against which the present compound has control activity may include, for example, insect pests, acarine pests and nematode pests. Specific examples are listed below:

Hemiptera: Delphacidae such as *Laodelphax striatellus*, *Nilaparvata lugens*, and *Sogatella furcifera*; Deltocephalidae such as *Nephotettix cincticeps* and *Empoasca onukii*; Aphididae such as *Aphis gossypii* and *Myzus persicae*;

Pentatomidae; Aleyrodidae such as *Trialeurodes vaporariorum, Bemisia tabaci,* and *Bemisia argentifolii; Coccidae;* Tingidae; Psyllidae;

Lepidoptera: Pyralidae such as *Chilo suppressalis, Cnaphalocrocis medinalis, Ostrinia nubilalis,* and *Parapediasia teterrella;* Noctuidae such as *Spodoptera litura, Spodoptera exigua, Pseudaletia separata, Mamestra brassicae, Agrotis ipsilon, Trichoplusia* spp., *Heliothis* spp., *Helicoverpa* spp., and *Earias* spp.; Pieridae such as *Pieris rapae crucivora;* Tortricidae such as *Adoxophyes orana fasciata, Grapholita molesta,* and *Cydia pomonella;* Carposinidae such as *Carposina niponensis;* Lyonetiidae such as *Lyonetia clerkella;* Gracillariidae such as *Phyllonorycter ringoniella;* Phyllocnistidae such as *Phyllocnistis citrella;* Yponomeutidae such as *Plutella xylostella;* Gelechiidae such as *Pectinophora gossypiella;* Arctiidae; Tineidae;

Diptera: Calicidae such as *Culex pipiens pallens, Culex tritaeniorhynchus,* and *Culex quinquefasciatus; Aedes* spp. such as *Aedes aegypti* and *Aedes albopictus; Anopheles* spp. such as *Anopheles Sinensis;* Chironomidae; Muscidae such as *Musca domestica* and *Muscina stabulans;* Calliphoridae; Sarcophagidae; Fanniidae; Anthomyiidae such as *Delia platura* and *Delia antiqua;* Tephritidae; Drosophilidae; Psychodidae; Tabanidae; Simuliidae; Stomoxyidae; Agromyzidae;

Coleoptera: *Diabrotica* spp. such as *Diabrotica virgifera virgifera* and *Diabrotica undecimpunctata howardi,* Scarabaeidae such as *Anomala cuprea* and *Anomala rufocuprea;* Curculionidae such as *Sitophilus zeamais, Lissorhoptrus oryzophilus,* and *Callosobruchus chinensis;* Tenebrionidae such as *Tenebrio molitor* and *Tribolium castaneum;* Chrysomelidae such as *Oulema oryzae, Aulacophora femoralis, Phyllotreta striolata,* and *Leptinotarsa decemlineata;* Anobiidae; *Epilachna* spp. such as *Epilachna vigintioctopunctata;* Lyctidae; Bostrychidae; Cerambycidae; *Paederus fuscipes;*

Thysanoptera: Thripidae spp. including *Thrips* spp. such as *Thrips palmi, Frankliniella* spp. such as *Frankliniella occidentalis,* and *Sciltothrips* spp. such as *Sciltothrips dorsalis;* Phlaeothripidae spp.;

Hymenoptera: Tenthredinidae; Formicidae; Vespidae;

Dictyoptera: *Periplaneta* spp.; *Blatta* spp.;

Orthoptera: Acrididae; Gryllotalpidae;

Aphaniptera: *Pulex irritans;*

Anoplura: *Pediculus humanus;*

Isoptera: Termitidae;

Acarina: Tetranychidae such as *Tetranychus urticae, Tetranychus kanzawai, Panonychus citri, Panonychus ulmi,* and *Oligonychus* spp.; Eriophyidae such as *Aculops pelekassi,* and *Aculus schlechtendali,* Tarsonemidae such as *Polyphagotarsonemus latus;* Tenuipalpidae; Tuckerellidae; Ixodidae such as *Haemaphysalis longicornis, Haemaphysalis flava, Dermacentor taiwanicus, Ixodes ovatus, Irodes persulcatus, Boophilus microplus,* and *Rhipicephalus sanguineus;* Acaridae such as *Trophagus putrescentiae;* Epidermoptidae such as *Dermatophagoides farinae, Dermatophagoides pteronyssinus;* Cheyletidae such as *Cheyletus eruditus, Cheyletus malaccensis, Cheyletus moorei,* Dermanyssidae;

Nematoda: *Pratylenchus coffeae, Pratylenchus fallax, Heterodera glycines, Globodera rostochiensis, Meloidogyne hapla,* and *Meloidogyne incognita.*

The pests controlling composition of the present invention contains the present compound and an inert carrier. Generally, the pests controlling composition of the present invention is a formulation obtained by mixing the present compound and a carrier such as a solid carrier, a liquid carrier and a gaseous carrier, and if necessary, adding a surfactant and other adjuvant for formulation. The formulation includes, for example, an oil solution, an emulsifiable concentration, a flowable formulation, a granule, a dust formulation, a wettable powder, a paste formulation, a microcapsule and the like. In the pests controlling composition of the present invention, the present compound is usually contained in an amount of 0.01% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol ethanol, isopropyl alcohol, butanol, hexanol, ethylene glycol), ethers (e.g., diethyl ether, diisopropyl ether, ethylene glycol dimethyl ether, diethylene glycol monomethyl ether, diethylene glycol monoethyl ether, propylene glycol monomethyl ether, tetrahydrofuran, dioxane), esters (e.g., ethyl acetate, butyl acetate), ketones (e.g., acetone, methyl ethyl ketone, methyl isobutyl ketone, cyclohexanone), nitriles (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil) and water.

The gaseous carrier for formulation includes, for example, butane gas, chlorofluorocarbons, liquefied petroleum gas (LPG), dimethyl ether, carbon dioxide and the like.

The surfactant for formulation includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-tert-butyl-4-methylphenol), BHA (a mixture of 2-tert-butyl-4-methoxyphenol and 3-t-butyl-4-methoxyphenol), vegetable oils, mineral oils, fatty acids, and fatty acid esters.

A base for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base.

Pests can be controlled by applying an effective amount of the present compound to pests directly and/or habitats of pests (e.g., nest, plant, soil). Usually the formulation containing the present invention is used as the present compound.

When the pests controlling composition of the present invention is used for a control of pests in agriculture and forestry, the application amount is usually 0.1 to 10,000 g as an active ingredient per 1,000 m$^2$. The emulsifiable concentrate, wettable powders, flowable formulation and microcapsule formulations are usually applied after dilution with water to have an active ingredient concentration of 10 to 10,000 ppm, while oil solution, dusts and granules are usually applied as such.

These formulations may be sprayed directly to the plant to be protected from pests. The pests living in a soil can be controlled by treating the soil with these formulations, and the formulations can also be applied to treat seedbeds prior to the planting plants or to treat planting holes or plant bottoms in the planting. Furthermore, the resin formulation shaped a sheet or cord of the pests controlling composition of the present invention can be applied by a method such as winding around plants, stretching in the vicinity of plants and laying on the soil surface at the plant bottom.

The pests controlling composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, organic phosphorus compounds such as fenitrothion, fenthion, pyridaphenthion, diazinon, chlorpyrifos, chlorpyrifos-methyl, acephate, methidathion, disulfoton, DDVP, sulprofos, profenofos, cyanophos, dioxabenzofos, dimethoate, phenthoate, malathion, trichlorfon, azinphosmethyl, monocrotophos, dicrotophos, ethion, fosthiazate and the like; carbamate compounds such as BPMC, benfuracarb, propoxur, carbosulfan, carbaryl, methomyl, ethiofencarb, aldicarb, oxamyl, fenothiocarb, thiodicarb, alanycarb and the like; pyrethroid compounds such as etofenprox, fenvalerate, esfenvalerate, fenpropathrin, cypermethrin, α-cypermethrin, Z-cypermethrin, permethrin, cyhalothrin, λ-cyhalothrin, cyfluthrin, β-cyfluthrin, deltamethrin, cycloprothrin, τ-fluvalinate, flucythrinate, bifenthrin, acrinathrin, tralomethrin, silafluofen, halfenprox and the like; neonicotinoid compounds such as thiamethoxam, dinotefuran, acetamiprid, clothianidin and the like; benzoylphenylurea compounds such as chlorfluazuron, teflubenzuron, flufenoxuron, lufenuron and the like; benzoylhydrazide compounds such as tebufenozide, halofenozide, methoxyfenozide, chromafenozide and the like; thiadiazine derivatives such as buprofezin and the like; nelicetoxin derivatives such as cartap, thiocyclam, bensultap and the like; chlorinated hydrocarbon compounds such as endosulfan, γ-BHC, 1,1-bis(chlorophenyl)-2,2,2-trichloroethanol and the like; formamidine derivatives such as amitraz, chlordimeform and the like; thiourea derivatives such as diafenthiuron and the like; phenylpyrazole compounds such as ethiprole, acetoprole and the like; chlorfenapyr pymetrozine, spinosad, indoxacarb, pyridalyl, pyriproxyfen, fenoxycarb, diofenolan, cyromazine, bromopropylate, tetradifon, quinomethionate, propargite, fenbutatin oxide, hexythiazox, etoxazole, clofentezine, pyridaben, fenpyroximate, tebufenpyrad, pyrimidifen, fenazaquin, acequinocyl, bifenazate, fluacrypyrim, milbemectin, avermectin, emamectin benzoate, azadirachtin [AZAD], polynactin complex [tetranactin, dinactin, trinactin] and the like.

The present invention will be further illustrated by the following production examples, formulation examples, and test examples; however, the present invention is not limited to these examples. First, production examples of the present compounds are exemplified.

In purification with silica gel column chromatography in the production examples and the reference production examples, Silica Gel 60 (produced by Merck) was used for silica gel, and a mixed solvent of hexane and ethyl acetate was used for eluent.

PRODUCTION EXAMPLE 1

In 4 ml of N,N-dimethylformamide was dissolved 333 mg of 5-chloro-3-methylthio-1,2,4-thiadiazole, and 142 mg of pyrrolidine was added dropwise at room temperature. The mixture was stirred for 6 hours. The reaction mixture was diluted with tert-butyl methyl ether, and extracted with tert-butyl methyl ether after the addition of 10% hydrochloric acid. The organic layer was washed with water, dried over anhydrous sodium sulfate, and concentrated under reduced pressure to obtain a crude 3-methylthio-5-(pyrrolidin-1-yl)-1,2,4-thiadiazole. In 4 ml of chloroform was added the crude 3-methylthio-5-(pyrrolidin-1-yl)-1,2,4-thiadiazole, and 1.52 g of 3-chloroperbenzoic acid (content: 65 weight %) was added under ice-cooling. The mixture was stirred at room temperature for 6 hours. The reaction mixture was washed with 10%-sodium sulfite aqueous solution and saturated sodium bicarbonate aqueous solution. The organic layer was dried over anhydrous sodium sulfate, and concentrated under reduced pressure to obtain a crude mixture of 3-methylsulfinyl-5-(pyrrolidin-1-yl)-1,2,4-thiadiazole and 3-methylsulfonyl-5-(pyrrolidin-1-yl)-1,2,4-thiadiazole. The crude mixture of 3-methylsulfinyl-5-(pyrrolidin-1-yl)-1,2,4-thiadiazole and 3-methylsulfonyl-5-(pyrrolidin-1-yl)-1,2,4-thiadiazole was mixed with 4 ml of N,N-dimethylformamide and 140 mg of 2-butyn-1-ol, and 120 mg sodium hydride (oil suspension; content: 60 weight %) under ice-cooling. The mixture was stirred for 15 minutes and at room temperature for 6 hours. The reaction mixture was extracted with tert-butyl methyl ether after the addition of saturated sodium chloride aqueous solution. The organic layer was dried over anhydrous sodium sulfate, and concentrated under reduced pressure. The residue was subjected to silica gel column chromatography to obtain 158 mg of 3-(2-butynyloxy)-5-(pyrrolidin-1-yl)-1,2,4-thiadiazole (hereinafter, referred to as the present compound (1)).

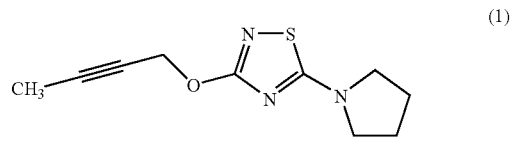

(1)

the present compound (1)

$^1$H-NMR (CDCl$_3$, TMS), δ (ppm): 4.90 (s, 2H), 3.42 (br, 4H), 2.06 (m, 4H), 1.85 (s, 3H)

EI-Mass: m/e=223(M$^+$)

PRODUCTION EXAMPLE 2

According to Production Example 1 except for using 168 mg of 2-pentyn-1-ol instead of 2-butyn-1-ol, obtained 173 mg of 3-(2-pentynyloxy)-5-(pyrrolidin-1-yl)-1,2,4-thiadiazole (hereinafter, referred to as the present compound (2)).

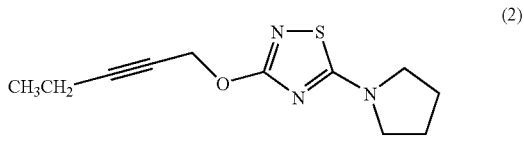

(2)

the present compound (2)
$^1$H-NMR (CDCl$_3$, TMS), δ (ppm): 4.91 (s, 2H), 3.43 (br, 4H), 2.22 (m, 2H), 2.05 (m, 4H), 1.15 (t, 3H)
EI-Mass: m/e=237(M$^+$)

PRODUCTION EXAMPLE 3

According to Production Example 1 except for using 170 mg of piperidine instead of pyrrolidine, obtained 147 mg of 3-(2-butynyloxy)-5-piperidino-1,2,4-thiadiazole (hereinafter, referred to as the present compound (3)).

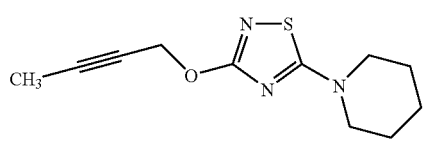

(3)

the present compound (3)
$^1$H-NMR (CDCl$_3$, TMS), δ (ppm): 4.89 (s, 2H), 3.43 (s, 4H), 1.85 (s, 3H), 1.67 (s, 6H)
EI-Mass: m/e=237(M$^+$)

PRODUCTION EXAMPLE 4

According to Production Example 1 except for using 168 mg of 2-pentyn-1-ol instead of pyrrolidine and using 170 mg of piperidine instead of 2-butyn-1-ol, obtained 155 mg of 3-(2-pentynyloxy)-5-piperidino-1,2,4-thiadiazole (hereinafter, referred to as the present compound (4)).

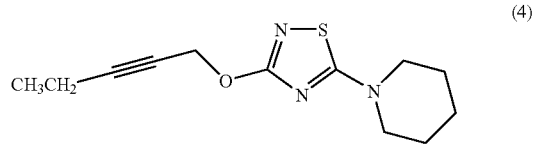

(4)

the present compound (4)
$^1$H-NMR (CDCl$_3$, TMS), δ (ppm): 4.90 (s, 2H), 3.43 (s, 4H), 2.21 (m, 2H), 1.66 (s, 6H), 1.13 (t, 3H)
EI-Mass: m/e=251(M$^+$)

PRODUCTION EXAMPLE 5

According to Production Example 1 except for using 198 mg of 2-methylpiperidine instead of pyrrolidine, obtained 133 mg of 3-(2-butynyloxy)-5-(2-methylpiperidino)-1,2,4-thiadiazole (hereinafter, referred to as the present compound (5)).

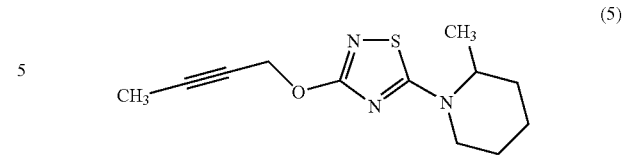

(5)

the present compound (5)
$^1$H-NMR (CDCl$_3$, TMS), δ (ppm): 4.89 (s, 2H)4.11 (br, 1H)3.63 (br, 1H)3.21 (t, 1H)1.86 (s, 3H)1.85-1.47 (m, 6H)1.26 (d, 3H)
EI-Mass: m/e=251(M$^+$)

PRODUCTION EXAMPLE 6

According to Production Example 1 except for using 168 mg of 2-pentyn-1-ol instead of 2-butyn-1-ol and using 198 mg of 2-methylpiperidine instead of pyrrolidine, obtained 144 mg of 3-(2-pentynyloxy)-5-(2-methylpiperidino)-1,2,4-thiadiazole (hereinafter, referred to as the present compound (6).

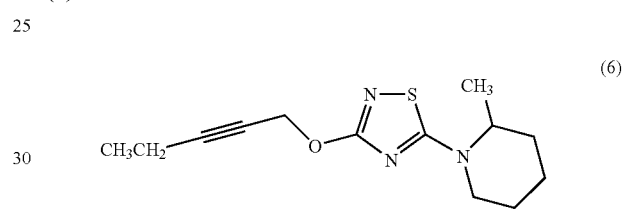

(6)

the present compound (6)
$^1$H-NMR (CDCl$_3$, TMS), δ (ppm): 4.91 (s, 2H), 4.12 (br, 1H), 3.61 (br, 1H), 3.20 (t, 1H), 2.24 (m, 2H), 1.82-1.47 (m, 4H), 1.26 (d, 3H), 1.13 (t, 3H)
EI-Mass: m/e=265(M$^+$)

PRODUCTION EXAMPLE 7

According to Production Example 1 except for using 198 mg 3-methylpyrrolidine instead of pyrrolidine, obtained 141 mg of 3-(2-butynyloxy)-5-(3-methylpiperidino)-1,2,4-thiadiazole (hereinafter, referred to as the present compound (7)).

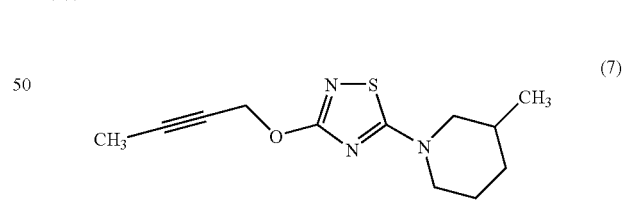

(7)

the present compound (7)
$^1$H-NMR (CDCl$_3$, TMS), δ (ppm): 4.89 (s, 2H), 3.72 (br, 2H), 3.06 (t, 1H), 2.72 (t, 1H), 1.86-1.55 (m, 7H), 1.15 (m, 1H), 0.94 (d, 3H)
EI-Mass: m/e=251(M$^+$)

PRODUCTION EXAMPLE 8

According to Production Example 1 except for using 168 mg of 2-pentyn-1-ol instead of 2-butyn-1-ol and 198 mg of 3-methylpiperidine using instead of pyrrolidine, obtained 145 mg of 3-(2-pentynyloxy)-5-(3-methylpiperidino)-1,2,4-thiadiazole (hereinafter, referred to as the present compound (8)).

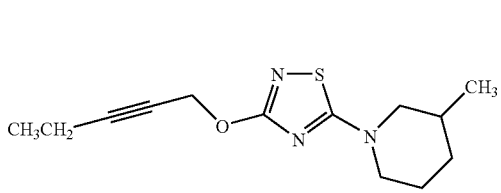

the present compound (8)

$^1$H-NMR (CDCl$_3$, TMS), δ (ppm): 4.91 (s, 2H), 3.73 (br, 2H), 3.05 (t, 1H), 2.72 (t, 1H), 2.22 (m, 2H), 1.89-1.54 (m, 4H), 1.21-1.06 (m, 4H), 0.94 (d, 3H)

EI-Mass: m/e=265(M$^+$)

PRODUCTION EXAMPLE 9

According to Production Example 1 except for using 174 mg of morpholine instead of pyrrolidine, obtained 82 mg of 3-(2-butynyloxy)-5-morpholino-1,2,4-thiadiazole (hereinafter, referred to as the present compound (9)).

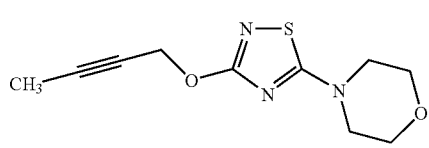

the present compound (9)

$^1$H-NMR (CDCl$_3$, TMS), δ (ppm): 4.89 (d, 2H), 3.78 (t, 4H), 3.47 (t, 4H), 1.85 (t, 3H)

PRODUCTION EXAMPLE 10

According to Production Example 1 except for using 168 mg of 2-pentyn-1-ol instead of 2-butyn-1-ol and using 174 mg of morpholine instead of pyrrolidine, obtained 83 mg of 3-(2-pentynyloxy)-5-morpholino-1,2,4-thiadiazole (hereinafter, referred to as the present compound (10)).

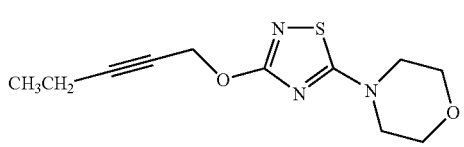

the present compound (10)

$^1$H-NMR (CDCl$_3$, TMS), δ (ppm): 4.91 (d, 2H), 3.78 (t, 4H), 3.48 (t, 4H), 2.22 (m, 2H), 1.15 (t, 3H)

PRODUCTION EXAMPLE 11

According to Production Example 1 except for using 198 mg of 4-methylpiperidine instead of pyrrolidine, obtained 175 mg of 3-(2-butynyloxy)-5-(4-methylpiperidino)-1,2,4-thiadiazole (hereinafter, referred to as the present compound (11)).

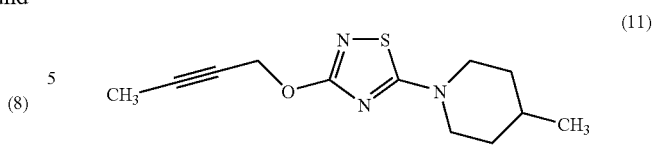

the present compound (11)

$^1$H-NMR (CDCl$_3$, TMS), δ (ppm): 4.89 (s, 2H), 3.81 (br, 2H), 3.09 (t, 2H), 1.87 (s, 3H), 1.76-1.56 (m, 3H), 1.28 (m, 2H), 0.98 (d, 3H)

EI-Mass: m/e=251(M$^+$)

PRODUCTION EXAMPLE 12

According to Production Example 1 except for using 168 mg of 2-pentyn-1-ol instead of 2-butyn-1-ol and using 198 mg of 4-methylpiperidine instead of pyrrolidine, obtained 207 mg of 3-(2-pentynyloxy)-5-(4-methylpiperidino)-1,2,4-thiadiazole (hereinafter, referred to as the present compound (12)).

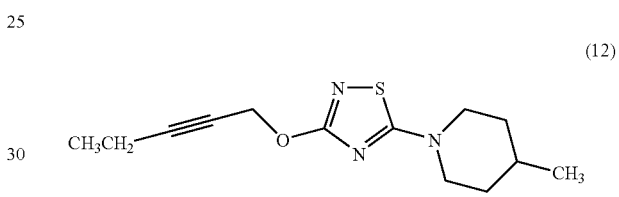

the present compound (12)

$^1$H-NMR (CDCl$_3$, TMS), δ (ppm): 4.90 (s, 2H), 3.80 (br, 2H), 3.08 (t, 2H), 2.24 (m, 2H), 1.78-1.58 (m, 3H), 1.26 (m, 2H), 1.13 (t, 3H), 0.98 (d, 3H)

EI-Mass: m/e=265(M$^+$)

PRODUCTION EXAMPLE 13

According to Production Example 1 except for using 198 mg of hexamethyleneimine instead of pyrrolidine, obtained 151 mg of 3-(2-butynyloxy)-5-hexamethyleneimino-1,2,4-thiadiazole (hereinafter, referred to as the present compound (13)).

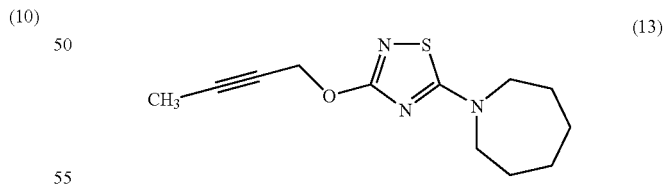

the present compound (13)

$^1$H-NMR (CDCl$_3$, TMS), δ (ppm): 4.89 (s, 2H), 3.71 (br, 2H), 3.28 (br, 2H), 1.86-1.74 (m, 7H), 1.61 (m, 4H)

EI-Mass: m/e=251(M$^+$)

PRODUCTION EXAMPLE 14

According to Production Example 1 except for using 168 mg of 2-pentyn-1-ol instead of 2-butyn-1-ol and 198 mg of hexamethyleneimine instead of pyrrolidine, obtained 150 mg of 3-(2-pentynyloxy)-5-hexamethyleneimino-1,2,4-thiadiazole (hereinafter, referred to as the present compound (14)).

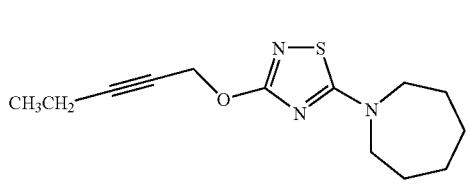
(14)

the present compound (14)
$^1$H-NMR (CDCl$_3$, TMS), δ (ppm): 4.90 (s, 2H), 3.92-3.08 (br, 4H), 2.23 (m, 2H), 1.83 (s, 4H), 1.62 (m, 4H), 1.15 (t, 3H)
EI-Mass: m/e=265(M$^+$)

PRODUCTION EXAMPLE 15

According to Production Example 1 except for using 226 mg of 3,5-dimethylpiperidine (a mixture of 8:2 geometrical isomers) instead of pyrrolidine, obtained 55 mg of one isomer of 3-(2-butynyloxy)-5-(3,5-dimethylpiperidino)-1,2,4-thiadiazole (relative low polarity with silica gel thin layer chromatography (hexane/ethyl acetate); hereinafter, referred to as the present compound (15a)) and 22 mg of another isomer (relative high polarity; hereinafter, referred to as the present compound (15b)).

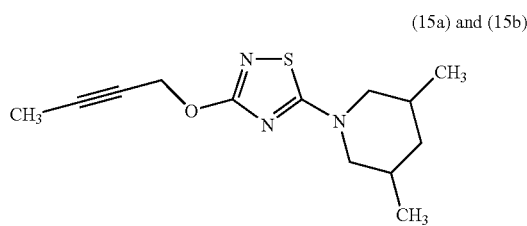
(15a) and (15b)

the present compound (15a)
m.p.: 104.4° C.
$^1$H-NMR (CDCl$_3$, TMS), δ (ppm): 4.89 (s, 2H), 3.74 (br, 2H), 2.57 (t, 2H), 1.92-1.70 (m, 6H), 0.92 (d, 6H), 0.81 (q, 1H)
EI-Mass: m/e=265 (M$^+$)

the present compound (15b)
$^1$H-NMR (CDCl$_3$, TMS), δ (ppm): 4.88 (s, 2H), 3.50 (br, 2H), 3.06 (br, 2H), 2.03 (m, 2H), 1.86 (s, 3H), 1.48 (m, 2H), 0.95 (m, 6H)
EI-Mass: m/e=265(M$^+$)

PRODUCTION EXAMPLE 16

According to Production Example 1 except for using 168 mg of 2-pentyn-1-ol instead of 2-butyn-1-ol and using 226 mg of 3,5-dimethylpiperidine (a mixture of 8:2 geometrical isomers) instead of pyrrolidine, obtained 57 mg of one isomer of 3-(2-pentynyloxy)-5-(3,5-dimethylpiperidino)-1,2,4-thiadiazole (relative low polarity with silica gel thin layer chromatography (hexane/ethyl acetate); hereinafter, referred to as the present compound (16a)) and 24 mg of another isomer (relative high polarity; hereinafter, referred to as the present compound (16b)).

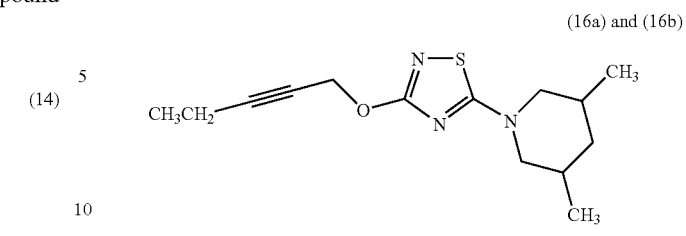
(16a) and (16b)

the present compound (16a)
$^1$H-NMR (CDCl$_3$, TMS), δ (ppm): 4.90 (s, 2H), 3.75 (br, 2H), 2.57 (t, 2H), 2.23 (m, 2H), 1.88-1.68 (m, 3H), 1.13 (t, 3H), 0.93 (d, 6H), 0.80 (q, 1H)
EI-Mass: m/e=279(M$^+$)

the present compound (16b)
$^1$H-NMR (CDCl$_3$, TMS), δ (ppm): 4.90 (s, 2H), 3.50 (br, 2H), 3.06 (br, 2H), 2.25 (m, 2H), 2.03 (m, 2H), 1.48 (t, 2H), 1.14 (t, 3H), 0.93 (d, 6H)
EI-Mass: m/e=279(M$^+$)

PRODUCTION EXAMPLE 17

According to Production Example 1 except for using 230 mg of 2,6-dimethylmorpholine (a mixture of geometrical isomers) instead of pyrrolidine, obtained 160 mg of one isomer of 3-(2-butynyloxy)-5-(2,6-dimethylmorpholino)-1,2,4-thiadiazole (relative low polarity with silica gel thin layer chromatography (hexane/ethyl acetate); hereinafter, referred to as the present compound (17a)) and 76 mg of another isomer (relative high polarity; hereinafter, referred to as the present compound (17b)).

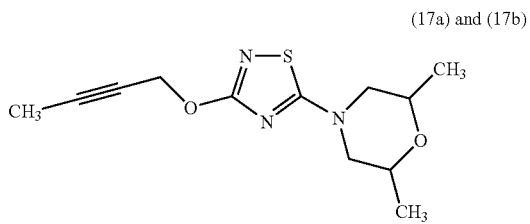
(17a) and (17b)

the present compound (17a)
$^1$H-NMR (CDCl$_3$, TMS), δ (ppm): 4.89 (s, 2H), 3.75-3.46 (m, 4H), 2.85 (dd, 2H), 1.85 (s, 3H), 1.21 (d, 6H)
EI-Mass: m/e=267(M$^+$)

the present compound (17b)
$^1$H-NMR (CDCl$_3$, TMS), δ (ppm): 4.89 (s, 2H), 4.08 (m, 2H), 3.54 (d, 2H), 3.16 (d, 2H), 1.86 (s, 3H), 1.24 (d, 6H)
EI-Mass: m/e=267(M$^+$)

PRODUCTION EXAMPLE 18

According to Production Example 1 except for using 168 mg of 2-pentyn-1-ol instead of 2-butyn-1-ol and using 235 mg of 2,6-dimethylmorpholine (a mixture of geometrical isomers) instead of pyrrolidine, obtained 172 mg of one isomer of 3-(2-pentynyloxy)-5-(2,6-dimethylmorpholino)-1,2,4-thiadiazole (relative low polarity with silica gel thin layer chromatography (hexane/ethyl acetate); hereinafter, referred to as the present compound (18a)) and 66 mg of another isomer (relative high polarity; hereinafter, referred to as the present compound (18b)).

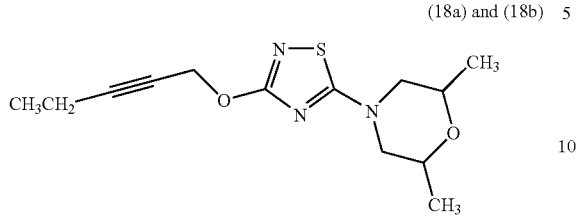
(18a) and (18b)

the present compound (18a)
$^1$H-NMR (CDCl$_3$, TMS), δ (ppm): 4.91 (d, 2H), 3.77-3.44 (m, 4H), 2.85 (t, 2H), 2.21 (m, 2H), 1.23 (m, 6H), 1.12 (t, 3H)
EI-Mass: m/e=281(M$^+$)

the present compound (18b)
$^1$H-NMR (CDCl$_3$, TMS), δ (ppm): 4.91 (t, 2H), 4.12 (m, 2H), 3.56 (m, 2H), 3.17 (m, 2H), 2.24 (m, 2H), 1.25 (d, 6H), 1.14 (t, 3H)
EI-Mass: m/e=281(M$^+$)

PRODUCTION EXAMPLE 19

In 6 ml of N,N-dimethylformamide were added 1.2 g of 3,5-diethylpiperidine, 500 mg of 5-chloro-3-methylthio-1,2,4-thiadiazole and 495 mg of potassium carbonate, and the mixture was stirred at room temperature for 3 hours. The reaction mixture was diluted with tert-butyl methyl ether, and extracted with tert-butyl methyl ether after the addition of 10% hydrochloric acid. The organic layer was washed with water, dried over anhydrous sodium sulfate, and concentrated under reduced pressure to obtain a crude 5-(3,5-diethylpiperidino)-3-methylthio-1,2,4-thiadiazole. In 6 ml of chloroform was added the crude 5-(3,5-diethylpiperidino)-3-methylthio-1,2,4-thiadiazole, and 1.76 g of 3-chloroperbenzoic acid (content: 65 weight %) was added under ice-cooling. The mixture was stirred at room temperature for 1 hour. The reaction mixture was washed with 10%-sodium sulfite aqueous solution and saturated sodium bicarbonate aqueous solution. The organic layer was dried over anhydrous sodium sulfate, and concentrated under reduced pressure to obtain a crude mixture of 5-(3,5-diethylpiperidino)-3-methylsulfinyl-1,2,4-thiadiazole and 5-(3,5-diethylpiperidino)-3-methylsulfonyl-1,2,4-thiadiazole. The crude mixture of 5-(3,5-diethylpiperidino)-3-methylsulfinyl-1,2,4-thiadiazole and 5-(3,5-diethylpiperidino)-3-methylsulfonyl-1,2,4-thiadiazole was mixed with 2 ml of N,N-dimethylformamide and 78 mg of 2-butyn-1-ol, and 55 mg of sodium hydride (oil suspension; content: 60 weight %) was added under ice-cooling. The mixture was stirred for 15 minutes and at room temperature for 2 hours. The reaction mixture extracted with tert-butyl methyl ether after the addition of saturated sodium chloride aqueous solution. The organic layer was dried over anhydrous sodium sulfate, and concentrated under reduced pressure. The residue was subjected to silica gel column chromatography to obtain 106 mg of one isomer of 3-(2-butynyloxy)-5-(3,5-diethylpiperidino)-1,2,4-thiadiazole (relative low polarity; hereinafter, referred to as the present compound (19a)) having a relative low polarity and 27 mg of another isomer (relative high polarity; hereinafter, referred to as the present compound (19b)) having a relative high polarity.

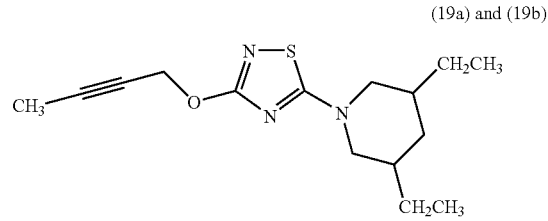
(19a) and (19b)

the present compound (19a)
m.p.: 47.7° C.
$^1$H-NMR (CDCl$_3$, TMS), δ (ppm): 4.80 (s, 2H), 3.81 (br, 2H), 2.61 (t, 2H), 1.98 (d, 1H), 1.87 (s, 3H), 1.58-1.44 (m, 2H), 1.36-1.21 (m, 4H), 0.94 (t, 6H), 0.72 (q, 1H) the present compound (19b)
$^1$H-NMR (CDCl$_3$, TMS), δ (ppm): 4.88 (s, 2H), 3.52 (br, 2H), 3.13 (br, 2H), 1.87 (s, 3H), 1.76-1.66 (m, 2H), 1.57-1.52 (m, 2H), 1.42-1.22 (m, 4H), 0.93 (t, 6H)

PRODUCTION EXAMPLE 20

In 3 ml of N,N-dimethylformamide were dissolved 373 mg of 3-methylsulfonyl-5-(3,5-dimethylpiperidino)-1,2,4-thiadiazole and 84 mg of 2-propyn-1-ol, and 71 mg of sodium hydride (oil suspension; content: 60 weight %) was added under ice-cooling. The mixture was stirred for 15 minutes and at room temperature for 1.5 hour. The reaction mixture was poured to water, and extracted with tert-butyl methyl ether. The organic layer was dried over anhydrous sodium sulfate, and concentrated under reduced pressure. The residue was subjected to silica gel column chromatography to obtain 326 mg of 3-(2-propynyloxy)-5-(3,5-dimethylpiperidino)-1,2,4-thiadiazole (hereinafter, referred to as the present compound (20)).

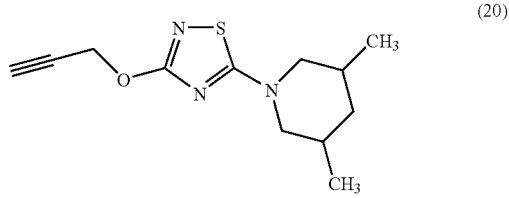
(20)

the present compound (20))
$^1$H-NMR (CDCl$_3$, TMS), δ (ppm): 4.93 (s, 2H), 3.74 (br, 1.6H), 3.51 (br, 0.4H), 3.06 (br, 0.4H), 2.60 (t, 1.6H), 2.49 (s, 1H), 2.05 (m, 0.4H), 1.83 (m, 0.8H), 1.75 (m, 1.6H), 1.50 (t, 0.4H), 0.98 (d, 1.8H), 0.95 (d, 4H), 0.87 (q, 0.8H)

PRODUCTION EXAMPLE 21

In 3 ml of N,N-dimethylformamide were dissolved 287 mg of 3-methylsulfinyl-5-(3,5-dimethylpiperidino)-1,2,4-thiadiazole and 103 mg of 3-pentyn-2-ol, and 58 mg of sodium hydride (oil suspension; content: 60 weight %) was added under ice-cooling. The mixture was stirred for 15 minutes and at room temperature for 1.5 hour. Furthermore, 30 mg of sodium hydride (oil suspension; content: 60 weight %) and 100 mg of 3-pentyn-2-ol were added in the mixture, and the mixture was stirred at room temperature for 30 minutes. The reaction mixture was diluted with tert-butyl methyl ether, and extracted with tert-butyl methyl ether after the addition of water. The organic layer was dried over anhydrous sodium sulfate, and concentrated under reduced pressure. The residue was subjected to silica gel column chromatography to obtain 297 mg of 3-(1-methyl-2-butynyloxy)-5-(3,5-dimethylpiperidino)-1,2,4-thiadiazole (hereinafter, referred to as the present compound (21)).

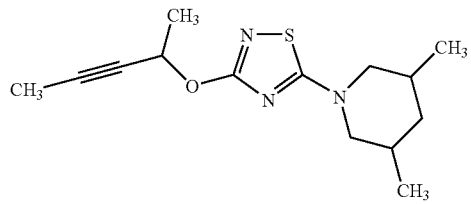
(21)

the present compound (21)

¹H-NMR (CDCl₃, TMS), δ (ppm): 5.47 (m, 1H), 3.76 (br, 1.6H), 3.52 (br, 0.4H), 3.05 (br, 0.4H), 2.57 (t, 1.6H), 2.02 (m, 0.4H), 1.87-1.67 (m, 2.4H), 1.84 (s, 3H), 1.59 (d, 3H), 1.49 (t, 0.4H), 0.96 (d, 1.2H), 0.92 (d, 4.8H), 0.81 (q, 0.8H)

PRODUCTION EXAMPLE 22

In 4 ml of tetrahydrofuran were dissolved 468 mg of the crude 3-methylsulfonyl-5-(3-trifluoromethylpiperidino)-1,2,4-thiadiazole obtained at Reference Production Example 4 and 105 mg of 2-butyn-1-ol, and 72 mg of sodium hydride (oil suspension; content: 60 weight %) was added under ice-cooling. The mixture was stirred at room temperature for 1.5 hour. The reaction mixture was extracted with ethyl acetate after the addition of water. The organic layer was dried over anhydrous sodium sulfate, and concentrated. The residue was subjected to silica gel column chromatography to obtain 366 mg of 3-(2-butynyloxy)-5-(3-trifluoromethylpiperidino)-1,2,4-thiadiazole (hereinafter, referred to as the present compound (22)).

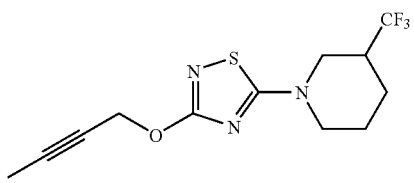
(22)

the present compound (22)

¹H-NMR (CDCl₃, TMS), δ (ppm): 4.91 (q, 2H), 4.90 (br, 1H), 4.89 (br, 1H), 3.10 (m, 2H), 2.40 (m, 1H), 2.12 (br, 1H), 1.87 (m, 4H), 1.73-1.22 (m, 2H)

PRODUCTION EXAMPLE 23

In 3 ml of tetrahydrofuran were dissolved 398 mg of 3-methylsulfonyl-5-(thiomorpholino)-1,2,4-thiadiazole and 180 mg of 2-butyn-1-ol, and 102 mg of sodium hydride (oil suspension; content: 60 weight %) was added at room temperature for 1 hour. The reaction mixture was concentrated. The residue was subjected to recrystallization from a mixed solvent of hexane-ethyl acetate to obtain 246 mg of 3-(2-butynyloxy)-5-thiomorpholino-1,2,4-thiadiazole (hereinafter, referred to as the present compound (23)).

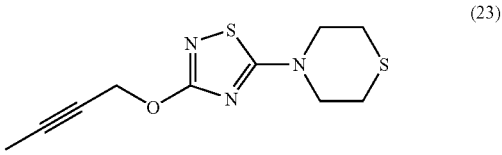
(23)

the present compound (23)

¹H-NMR (CDCl₃, TMS), δ (ppm): 4.89 (s, 2H), 3.79 (m, 4H), 2.71 (m, 4H), 1.86 (s, 3H)

Next, production examples of the intermediate compounds of the present compound are exemplified.

Reference Production Example 1

In 9 ml of N,N-dimethylformamide was dissolved 740 mg of 5-chloro-3-methylthio-1,2,4-thiadiazole, and 1.25 g of 3,5-dimethylpiperidine (a mixture of 8:2 geometrical isomers) was added dropwise under ice-cooling. The mixture was stirred at room temperature for 20 minutes. The reaction mixture was diluted with tert-butyl methyl ether, and extracted with tert-butyl methyl ether after the addition of 10% hydrochloric acid. The organic layer was dried over anhydrous sodium sulfate, and concentrated under reduced pressure. The residue was subjected to silica gel column chromatography to obtain 860 mg of 3-methylthio-5-(3,5-dimethylpiperidino)-1,2,4-thiadiazole.

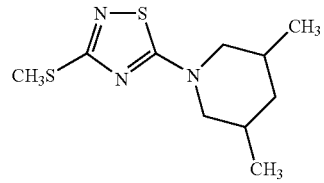

3-methylthio-5-(3,5-dimethylpiperidino)-1,2,4-thiadiazole

¹H-NMR (CDCl₃, TMS), δ (ppm): 3.76 (br, 1.6H), 1.57 (br, 0.4H), 3.06 (m, 0.4H), 2.62 (t, 1.6H), 2.59 (s, 3H), 2.04 (m, 0.4H), 1.88-1.68 (m, 2.4H), 1.49 (t, 0.4H), 0.98 (d, 1.2H), 0.93 (d, 4.8H), 0.81 (q, 0.8H)

Reference Production Example 2

The 3-methylthio-5-(3,5-dimethylpiperidino)-1,2,4-thiadiazole obtained at Reference Production Example 1 was mixed with 10 ml of chloroform, and 1.41 g of 3-chloroperbenzoic acid (content: 65 weight %) under ice-cooling. The mixture was stirred at room temperature for 2 hours and left as it was for 16 hours. The reaction mixture was extracted with chloroform after the addition of saturated sodium bicarbonate aqueous solution. The organic layer was dried over anhydrous sodium sulfate, and concentrated under reduced pressure. The residue was subjected to silica gel column chromatography to obtain 373 mg of 3-methylsulfonyl-5-(3,5-dimethylpiperidino)-1,2,4-thiadiazole and 287 mg of 3-methylsulfinyl-5-(3,5-dimethylpiperidino)-1,2,4-thiadiazole.

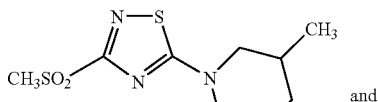

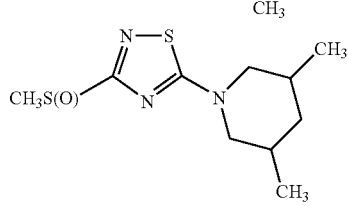

3-methylsulfonyl-3-(3,5-dimethylpiperidino)-1,2,4-thiadiazole
white solid
$^1$H-NMR (CDCl$_3$, TMS), δ (ppm): 3.68 (br), 3.23 (s, 3H), 3.10 (br), 2.70 (br), 2.08 (m), 1.92-1.64 (m), 1.49-1.43 (m), 1.01-1.70 (m)

3-methylsulfinyl-3-(3,5-dimethylpiperidino)-1,2,4-thiadiazole
oil
$^1$H-NMR (CDCl$_3$, TMS), δ (ppm): 3.76 (br), 3.14 (br), 2.96 (s, 3H), 2.68 (m), 2.08 (m), 1.92-1.70 (m), 1.53 (t), 1.01-0.95 (m), 0.85 (q)

Reference Production Example 3

In 3 ml of tetrahydrofuran were added 376 mg of 5-chloro-3-methylthio-1,2,4-thiadiazole, 230 mg of 3-trifluoromethylpiperidine and 1.52 g of triethylamine at room temperature. The mixture was stirred for 1.5 hour under reflux condition, and left as it for 14 hours at room temperature. The reaction mixture was extracted with ethyl acetate after the addition of water. The organic layer was dried over anhydrous sodium sulfate, and concentrated under reduced pressure. The residue was subjected to silica gel column chromatography to obtain 398 mg of 3-methylthio-5-(3-trifluoromethylpiperidino)-1,2,4-thiadiazole.

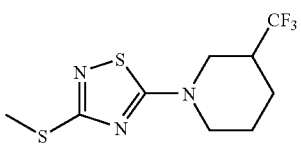

3-methylthio-5-(3-trifluoromethylpiperidino)-1,2,4-thiadiazole
$^1$H-NMR (CDCl$_3$, TMS), δ (ppm): 4.17 (br, 1H), 3.74 (br, 1H), 3.13 (m, 2H), 2.59 (s, 3H), 2.40 (m, 1H), 2.12 (m, 1H), 1.90 (m, 1H), 1.74-1.23 (m, 2H)

Reference Production Example 4

The 3-methylthio-5-(3-trifluoromethylpiperidino)-1,2,4-thiadiazole obtained at Reference Production Example 3 was mixed with 4 ml of chloroform, and 870 mg of 3-chloroperbenzoic acid (content: 70-75 weight %) under ice-cooling. The mixture was stirred at room temperature for 1.25 hours. The reaction mixture was extracted with chloroform after the addition of 10% sodium sulfite aqueous solution. The organic layer was washed with saturated sodium bicarbonate aqueous solution, dried over anhydrous sodium sulfate, and concentrated under reduced pressure to obtain 468 mg of crude 3-methylsulfonyl-3-(3-trifluoromethylpiperidino)-1,2,4-thiadiazole.

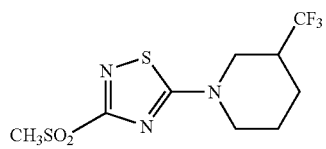

3-methylsulfonyl-3-(3-trifluoromethylpiperidino)-1,2,4-thiadiazole
$^1$H-NMR (CDCl$_3$, TMS), δ (ppm): 4.23 (br, 1H), 3.83 (br, 1H), 3.29 (m, 5H) 2.45 (m, 1H), 2.17 (m, 1H), 1.97 (m, 1H), 1.78-1.27 (m, 2H)

Reference Production Example 5

With 12 ml of chloroform was mixed 1.0 g of 5-chloro-3-methylthio-1,2,4-thiadiazole, and 2.59 g of 3-chloroperbenzoic acid (content: 70-75 weight %) was added under ice-cooling. The mixture was stirred at room temperature for 2.25 hours and left as it was for 15 hours to obtain a crude mixture of 5-chloro-3-methylsulfonyl-1,2,4-thiadiazole and 5-chloro-3-methylsulfinyl-1,2,4-thiadiazole. Into the crude mixture of 5-chloro-3-methylsulfonyl-1,2,4-thiadiazole and 5-chloro-3-methylsulfinyl-1,2,4-thiadiazole was added 2.46 g of thiomorpholine dropwise under water-cooling. The mixture was stirred for 1 hour at room temperature. The reaction mixture was extracted with chloroform after the addition of saturated sodium bicarbonate aqueous solution. The organic layer was dried over anhydrous sodium sulfate, and concentrated under reduced pressure. The residue was subjected to silica gel column chromatography to obtain 1.08 g of 3-methylsulfonyl-5-thiomorpholino-1,2,4-thiadiazole and 6 mg of 3-methylsulfinyl-5-thiomorpholino-1,2,4-thiadiazole.

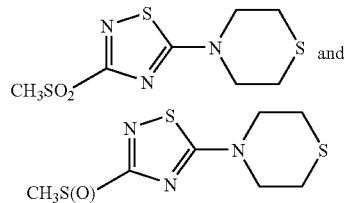

3-methylsulfonyl-5-thiomorpholino-1,2,4-thiadiazole
$^1$H-NMR (CDCl$_3$, TMS), δ (ppm): 3.90 (br, 4H), 3.28 (s, 3H), 2.76 (m, 4H) 3-methylsulfinyl-5-thiomorpholino-1,2,4-thiadiazole
$^1$H-NMR (CDCl$_3$, TMS), δ (ppm): 3.89 (br, 4H), 2.77 (s, 3H), 2.76 (m, 4H)

Formulation Examples are exemplified below. In addition, "part" means a part by weight. The present compounds are designated by their compound numbers shown above.

Formulation Example 1

In 37.5 parts of xylene and 37.5 parts of dimethylformamide are dissolved 9 parts of each of the present compounds (1), (2), (3), (4), (5), (6), (7), (8), (9), (10), (11), (12), (13), (14), (15a), (15b), (16a), (16b), (17a), (17b), (18a), (18b), (19a), (19b), (20), (21), (22) and (23), and 10 parts of polyoxyethylene styryl phenyl ether and 6 parts of calcium dodecylbenzenesulfonate are added thereto, followed by well stirring and mixing, to give an emulsifiable concentrate for each compound.

Formulation Example 2

In a mixture containing 4 parts of sodium laurylsulfate, 2 parts of calcium ligninsulfonate, 20 parts of synthetic hydrated silicone oxide fine powder and 65 parts of diatomaceous earth is added 9 parts of each of the present compounds (1), (2), (3), (4), (5), (6), (7), (8), (9), (10), (11), (12), (13), (14), (15a), (15b), (16a), (16b), (17a), (17b), (18a), (18b), (19a), (19b), (20), (21), (22) and (23), followed by well stirring and mixing, to give a wettable powder for each compound.

Formulation Example 3

In a mixture containing 5 parts of synthetic hydrated silicon oxide fine powder, 5 parts of sodium dodecylbenzenesulfonate, 30 parts of bentonite and 57 parts of clay are added 3 parts of each of the present compounds (1), (2), (3), (4), (5), (6), (7), (8), (9), (10), (11), (12), (13), (14), (15a), (15b), (16a), (16b), (17a), (17b), (18a), (18b), (19a), (19b), (20), (21), (22) and (23), followed by well stirring and mixing. Then an appropriate amount of water is added to this mixture, followed by further stirring, granulating with a granulator and air drying, to give a granule for each compound.

Formulation Example 4

4.5 Parts of each of the present compounds (1), (2), (3), (4), (5), (6), (7), (8), (9), (10), (11), (12), (13), (14), (15a), (15b), (16a), (16b), (17a), (17b), (18a), (18b), (19a), (19b), (20), (21), (22) and (23), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture is added 86.5 parts of cut clay, followed by well stirring and mixing, to give a powder for each compound.

Formulation Example 5

10 Parts of each of the present compounds (1), (2), (3), (4), (5), (6), (7), (8), (9), (10), (11), (12), (13), (14), (15a), (15b), (16a), (16b), (17a), (17b), (18a), (18b), (19a), (19b), (20), (21), (22) and (23), 35 parts of white carbon containing 50 parts of polyoxyethylene alkyl ether sulfate ammonium salt and 55 parts of water are mixed and pulverized by the wet grinding method to give a formulation for each compound.

The following test example will demonstrate that the present compounds are useful as active ingredient of pests controlling composition.

Test Example 1

The formulation of each of the present compounds (3), (4), (5), (6), (7), (8), (9), (10), (11), (14), (15a), (15b), (16a), (17a), (17b), (18a), (18b), (19), (20), (21) and (22) according to Formulation Example 5 was diluted with water so that the active ingredient concentration came to 500 ppm to prepare a spray liquid.

The seeds of cucumber were planted in a polyethylene cup and it was grown until the first true leaf was developed. On the plant about twenty *Aphis gossypii* (cotton aphid) are allowed to be parasitic. On the next day, the above spray liquid was applied at a ratio of 20 ml/cup to the cucumber plant. On the sixth day after the application, the number of *Aphis gossypii* was examined, and the control value was determined by the following formula:

Control value (%)={1−($Cb \times Tai$)/($Cai \times Tb$)}×100 wherein the variables in the formula have the following meanings:

Cb: the number of insects before the treatment in the non-treated area;

Cai: the number of insects at the time of observation in the non-treated area;

Tb: the number of insects before the treatment in the treated area; and

Tai: the number of insects at the time of observation in the treated area.

As a result, the present compounds (3), (4), (5), (6), (7), (8), (9), (10), (11), (14), (15a), (15b), (16a), (17a), (17b), (18a), (18b), (19), (20), (21) and (22) had the control value of 90% or higher.

Test Example 2

The formulation of each present compound (4), (5), (6), (7), (8), (11), (12), (13), (14), (15a), (15b), (16a), (16b), (17a), (18a), (19), (20), (21) and (22) according to Formulation Example 5 was diluted with water so that the active ingredient concentration came to 500 ppm to prepare a spray solution.

The seeds of cabbage were planted in a polyethylene cup and grown until their first true leaf was developed. The first foliage leaf was left and the other leaves were cut off. Some adults of *Bemisia argentifolii* (silverleaf whitefly) were set free on the cabbage plants and allowed to lay eggs for about 24 hours. The cabbage plants with about 80 to 100 eggs thus laid were left in a greenhouse for 8 days, and the above spray liquid was applied at a ratio of 20 ml/cup to the cabbage plant with larvae being hatched from the laid eggs. On the seventh day after the application, the number of surviving larvae was counted.

As a result, for the present compounds (4), (5), (6), (7), (8), (11), (12), (13), (14), (15a), (15b), (16a), (16b), (17a), (18a), (19), (20), (21) and (22), the number of surviving larvae on the cabbage leaves treated with each of these compounds was not greater than 10.

Test Example 3

The formulation of each of the present compounds (4), (5), (6), (7), (8), (12), (17a) and (18a) according to Formulation Example 5 was diluted with water so that the active ingredient concentration came to 500 ppm to prepare a spray liquid.

Fifty grams of molding (Bonsoru 2; available from Sumitomo Chemical Co., Ltd.) was put into a polyethylene cup, and 10 to 15 seeds of rice were planted in the polyethylene cup. The rice plants were grown until the second foliage leaves developed and then cut into the same height of 5 cm. The test spray liquid, which had been prepared as described above, was applied at a ratio of 20 ml/cup onto these rice plants. After the spray liquid sprayed onto the rice plants was dried, thirty first-instar larvae of *Nilaparvata lugens* (brown planthopper) were set free on the rice plants, which were then left in a greenhouse at 25° C. On the 6th day after the release of larvae of *Nilaparvata lugens*, the number of *Nilaparvata lugens* parasitic on the rice plants was examined.

As a result, in the treatment with each of the present compounds (4), (5), (6), (7), (8), (12), (17a) and (18a), the number of parasitic insects on the 6th day after the treatment was not greater than 3.

INDUSTRIAL APPLICABILITY

The present compound can effectively control pests such as insect pests, acarine pests and the like.

The invention claimed is:

1. A 1,2,4-thiadiazole compound of the formula (I):

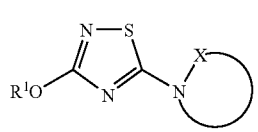

wherein $R^1$ represents C3-C7 alkynyl; X represents C4-C7 straight alkylene optionally substituted with one to four of $R^2$, C4-C7 straight alkenylene optionally substituted with one to four of $R^2$, ethylene-oxy-ethylene optionally substituted with one to four of $R^4$, or ethylene-thio-ethylene optionally substituted with one to four of $R^4$; $R^2$ represents a halogen atom, trifluoromethyl or C1-C4 alkyl; and $R^4$ represents a fluorine atom or C1-C3 alkyl.

2. The 1,2,4-thiadiazole compound according to claim 1, wherein X is $C^4$-C7 straight alkylene optionally substituted with one to four of $R^2$, C4-C7 straight alkenylene optionally substituted with one to four of $R^2$, or ethylene-oxy-ethylene optionally substituted with one or two of $R^4$; $R^2$ is a halogen atom, trifluoromethyl or C1-C4 alkyl; and $R^4$ is C1-C3 alkyl.

3. The 1,2,4-thiadiazole compound according to claim 1, wherein X is C4-C7 straight alkylene optionally substituted with one to four of $R^2$; and $R^2$ is a halogen atom, trifluoromethyl or C1-C4 alkyl.

4. The 1,2,4-thiadiazole compound according to claim 1, wherein X is ethylene-oxy-ethylene optionally substituted with one to four of $R^4$; and $R^4$ is C1-C4 alkyl.

5. The 1,2,4-thiadiazole compound according to claim 1, wherein $R^1$ is 2-propynyl, 2-butynyl, 1-methyl-2-butynyl, 2-pentynyl, 4,4-dimethyl-2-pentynyl, 1-methyl-2-propynyl or 1,1-dimethyl-2-propynyl.

6. A pests controlling composition containing an effective amount of the 1,2,4-thiadiazole compound according to claim 1 as an active ingredient and a carrier.

7. A method for controlling pests comprising applying an effective amount of the 1,2,4-thiadiazole compound according to claim 1 to pests or habitat of pests.

8. A 1,2,4-thiadiazole compound of the formula (II):

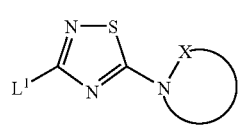

wherein $L^1$ represents methylsulfinyl or methylsulfonyl; X represents C4-C7 straight alikylene optionally substituted with one to four of $R^2$, C4-C7 straight alkenylene optionally substituted with one to four of $R^2$, ethylene-oxy-ethylene optionally substituted with one to four of $R^4$, or ethylene-thio-ethylene optionally substituted with one to four of $R^4$; $R^2$ represents a halogen atom, trifluoromethyl or C1-C4 alkyl; and $R^4$ represents a fluorine atom or C1-C3 alkyl.

9. The 1,2,4-thiadiazole compound according to claim 8, wherein X is C4-C7 straight alkylene optionally substituted with one to four of $R^2$, C4-C7 straight alkenylene optionally substituted with one to four of $R^2$, or ethylene-oxy-ethylene optionally substituted with one or two of $R^4$; $R^2$ is a halogen atom, trifluoromethyl or C1-C4 alkyl; and $R^4$ is C1-C3 alkyl.

* * * * *